United States Patent [19]

Shelton

[11] 4,261,388

[45] Apr. 14, 1981

[54] DROP RATE CONTROLLER

[75] Inventor: Christopher D. Shelton, London, England

[73] Assignee: Frenshore Ltd., London, England

[21] Appl. No.: 39,238

[22] Filed: May 15, 1979

[30] Foreign Application Priority Data

May 19, 1978 [GB] United Kingdom ............. 20713/78

[51] Int. Cl.³ .............................................. A61M 5/16
[52] U.S. Cl. ................................ 137/486; 137/487.5; 251/6
[58] Field of Search .................. 137/486, 487.5; 251/6

[56] References Cited

U.S. PATENT DOCUMENTS

| | | | |
|---|---|---|---|
| 3,163,176 | 12/1964 | Darling | 137/487.5 |
| 3,289,999 | 12/1966 | Konzak | 251/6 |
| 3,450,153 | 6/1969 | Hildebrandt | 137/487.5 X |
| 4,038,982 | 8/1977 | Burke | 137/487.5 X |

Primary Examiner—Alan Cohan
Attorney, Agent, or Firm—Steele, Gould & Fried

[57] ABSTRACT

A liquid drop rate controller for controlling flow of fluid from an infusion fluid reservoir to an intravenous infusion site which includes a cam means in the form of a wheel mounted eccentrically on a shaft which varies the compression on a flexible tube carrying the liquid; the controller senses the actual drip rate optically and compares this to a preselected desired drip rate and varies the compression accordingly. The comparison is accomplished electronically by the generation of a time base whose frequency is controlled by the selected drip rate; this time base is compared to the actual drip rate observed by the optical sensing means, and the cam means is controlled in relation to an error signal obtained through the comparison. The controller includes a separate comparison circuit which comes into operation at low drip rates so as to increase accuracy of control.

14 Claims, 6 Drawing Figures

DROP RATE CONTROLLER

BACKGROUND OF THE INVENTION

1. Field of the Invention

This invention relates to a liquid drop rate controller for controlling the flow of liquid from an infusion fluid reservoir (such as a drip-bottle or bag) to an intravenous or other infusion site of a patient in medical care.

2. Description of the Prior Art

Several types of drop rate controller are known whereby the rate of liquid infused into a patient may be variably controlled and maintained at a preselected rate. A common type of controller involves variation in the rate of pumping of the liquid along a flexible tube between the liquid reservoir and the patient. Typically the pumping action is provided by a peristatic pump, the motor of which is electronically controlled in relation to a desired, preset liquid supply rate. The latter rate is commonly expressed as a drip-rate, with a specific number of drips per unit time being set as the desired liquid supply rate. A control of the drip-rate by means of a pumping action has proved popular since pumps are generally easy to control electronically whereby to supply desired liquid supply rates, but currently a pumping action of infusion liquid into the human body is meeting with resistance in some medical circles, who advocate that a gravity-feed infusion system is safer and more reliable. Unfortunately electronic control of gravity feed mechanisms which do not introduce an element of pumping to the liquid are not easy to design.

Despite difficulties, some electronically-operating gravity-feed infusion controllers do exist. A typical one is the Series 200 Infusion Controller produced by Ivac Corporation, U.S.A. This controller senses the drip-rate of drops as they fall under gravity from a drip reservoir (e.g. a bag) into a chamber holding a head of the liquid. The liquid subsequently passes through a flow restrictor to the patient. Should the hydrostatic pressure of the liquid being infused alter (for example as a consequence of a change in the intravenous back-pressure from the patient's blood system) and the drip-rate change in consequence, the change in drip-rate is sensed by the controller and the hydraulic impedance of the flow restrictor altered to restore the drip-rate to its preset level. The hydraulic impedance of the flow restrictor is essentially created by mechanically compressing a flexible tube through which the liquid passes, the compression being converted from electrical signals to mechanical compression through a solenoid. The solenoid is continuously pulsed with power and thus the compression supplied to the tube is a continuous mechanical pulsing of the tube. The hydraulic impedance is changed by altering the electrical pulse signals supplied to the solenoid and thus altering the frequency/pulse width of the mechanical pulses compressing the tube.

One disadvantage of the present gravity-feed infusion controllers is that the dynamic range of preset drip-rates over which they can operate is not wide and, especially, they do not operate efficiently or at all at very low drip-rates.

SUMMARY OF THE INVENTION

An object of the invention is to provide a gravity feed infusion controller where the liquid flow rate may be metered accurately, especially at low flow rates, and which is also economic to produce.

In a first aspect of the invention there is provided an infusion drop rate controller comprising a means for sensing the drip rate of liquid from an infusion liquid reservoir, a means for selecting and storing a desired drip rate, a means for varying the hydraulic impedance formed from a flexible tube in a flow line from said reservoir, and a means for controlling said varying means in response to the sensed drip rate to maintain the flow of liquid to the selected and stored drip rate, wherein the varying means comprises a cam means mounted on a shaft for compressing said flexible tube against an anvil member whereby rotation of said shaft varies the extent of compression to vary said hydraulic impedance.

DESCRIPTION OF THE DRAWINGS

Preferred features of the invention will be described with reference to the accompanying drawings, given by way of example, in which.

DESCRIPTION OF THE PREFERRED EMBODIMENT

Figure 1:
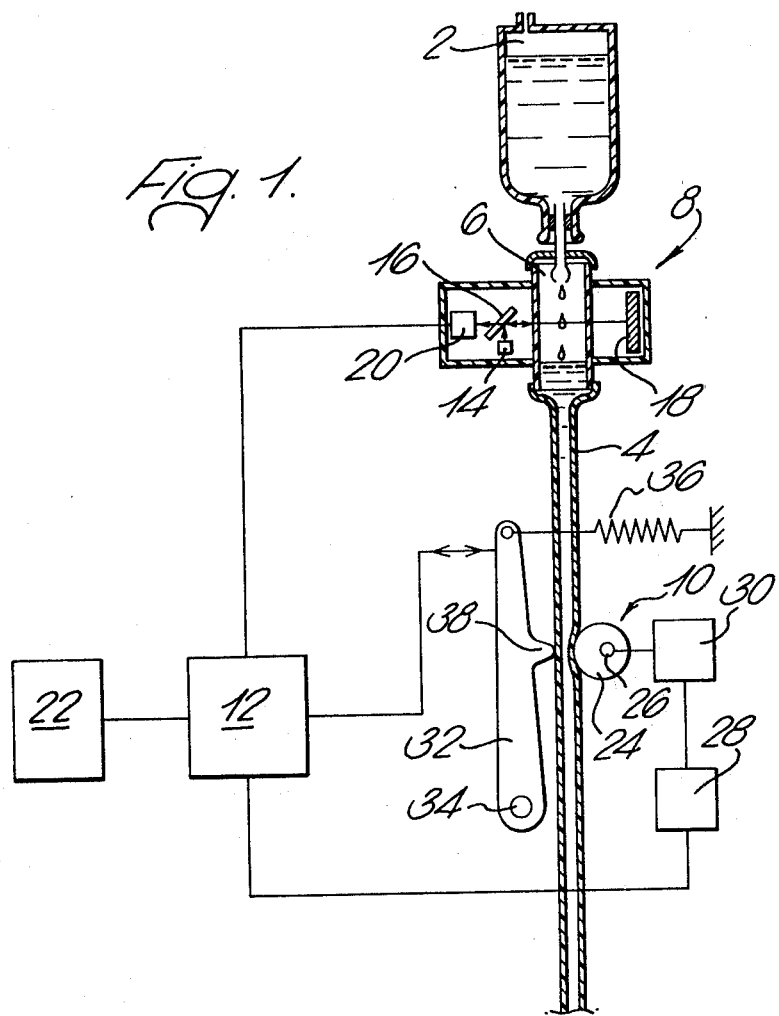
FIG. 1 is a schematic side view of a preferred drop rate controller according to the invention.

Referring to FIG. 1, the preferred drop rate controller is shown set up in combination with a liquid reservoir (bottle) 2 of liquid to be infused through a flexible plastics tubing 4 to a patient (not shown). The tubing 4 is supplied with liquid from a drip chamber 6 which is maintained with a head of liquid, replenished drip by drip from reservoir 2. The drip rate controller comprises three essential elements: a drip-rate detector 8, a flow restrictor 10, and electronic processing and control means 12 for controlling the flow restrictor 10 in response to the output of detector 8 and a desired, preset drip rate.

The drip-rate detector 8 comprises a light source 14, half-silvered mirror 16, a retroreflector 18, and a phototransistor 20. Signals from the phototransistor 20 are supplied to the processing and control means 12 described in more detail below.

Thumbwheel switches 22 are employed by the operator to set a desired drip rate and the value held by the switches is also fed to the processing and control means 12.

The flow restrictor 10 comprises a wheel 24 mounted eccentrically on a shaft 26 which is driven by a motor 28 through a high reduction gearbox 30. A compression lever 32 is provided on the side of tubing 4 to oppose wheel 24, pivots about a pivot shaft 34 and is biassed towards wheel 24 by means of a spring 36. The compression lever 32 is provided with a stub arm 38 which contacts the tubing 4 at a point opposite to the point of contact of wheel 24 with tubing 4. The position of compression lever 32 relative to tubing 4, and the amount of compression (if any) provided thereto is controlled from the processing and control means 12 by a solenoid and latch mechanism not shown in FIG. 1 but described in more detail below.

In operation, the thumbwheel switches 22 are set to a desired drip-rate and compression lever 32 latched back so as to contact but not compress substantially tubing 4.

As the drops of liquid fall into drip chamber 6 they interrupt the light beam provided by light source 14 and modulate the signal provided by phototransistor 20 to the processing and control means 12. The rate of modulation (and thus the drip rate from reservoir 2) is computed by processing and control means 12, compared to the desired drip-rate set by the switches 22 and the motor 28 actuated accordingly. Since the wheel 24 is eccentrically mounted on shaft 26, rotation of the latter through the motor 28 and gearbox 30 will, at different angular positions, cause the wheel to compress the flexible tubing 4 to different extents against stub arm 38 which acts as an anvil for the compression provided by wheel 24, thus exercising control of the actual flow rate of liquid supplied to the patient. Thus, if the intravenous back pressure from the patient suddenly increases and causes the drip-rate from reservoir 2 to slow, the control means 12 senses this deceleration of fluid supply and actuates motor 28 to ease slightly the compression of wheel 24 on tubing 4. This reduces the hydraulic impedance provided at the point of compression and thus enables the preset drip-rate to be restored.

In the event of a failure of the control apparatus, e.g. a loss of power, then the latch holding back compression lever 32 is automatically released and the bias provided by spring 36 causes the stub arm 38 to compress fully the tubing 4 against wheel 24 and shut off the supply of liquid to the patient until the fault is rectified or power restored. Furthermore, in the event of a dangerously high drip rate being sensed by the processing and control means 12, the latter sends an appropriate signal to the solenoid controlling the latch. This also causes the latch to release and cut off the flow of liquid to the patient.

Figure 3:
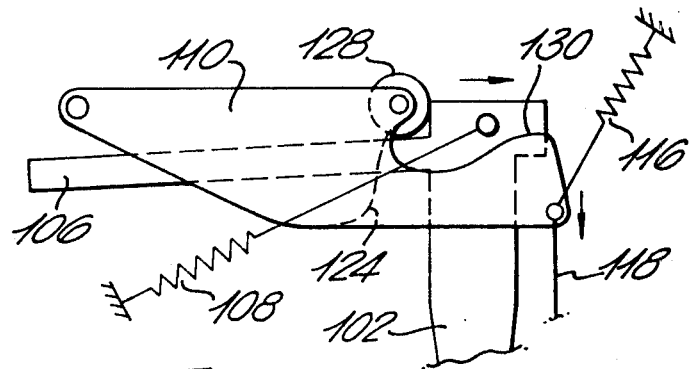
Figure 4:
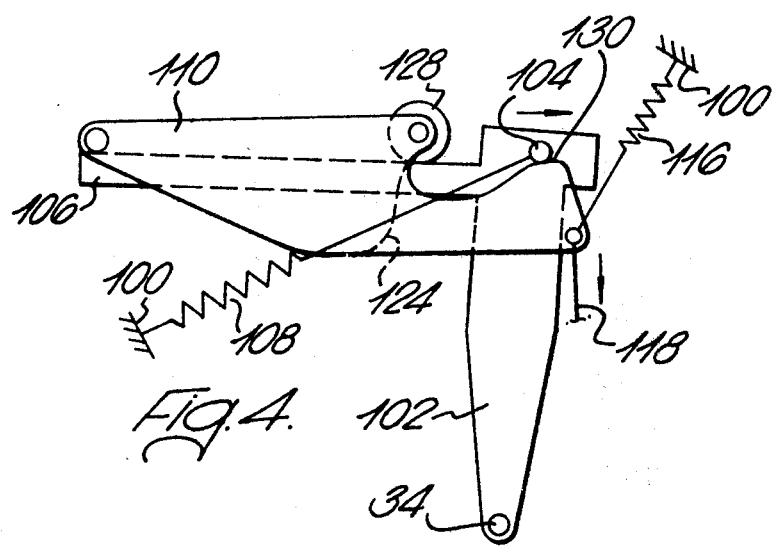
Figure 5:
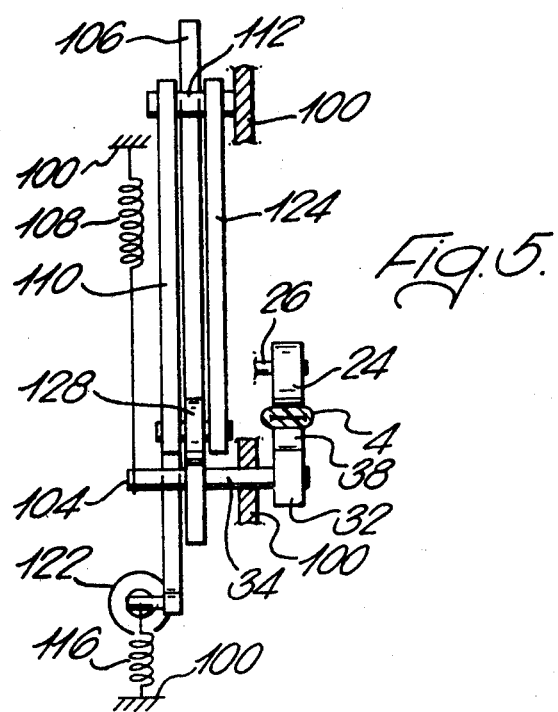
FIG. 5 is a plan view looking down onto the latching mechanism shown in FIG. 2.

The latching mechanism for the compression lever 32 will now be described with reference to FIGS. 2 to 5. The compression lever 32 and wheel 24 shown in FIG. 1 are mounted on the exterior of a housing 100 for the apparatus and the shaft 34 passes through the housing 100. Inside the housing a latching arm 102 is fixedly mounted on shaft 34 and moves in unison with compression lever 32. The latching arm 102 is provided with a pin 104 and a guide arm 106. A spring 108 extends between the housing 100 and pin 104 and biasses the latching arm to the left as seen in FIGS. 2 to 4.

A latching member 110 is pivotally mounted on a shaft 112 extending within housing 100 and has mounted thereon a pin 114. A spring 116 extends between housing 100 and pin 114 and a rod 118 extends downwardly to a plunger 120 of a solenoid 122.

Figure 2:
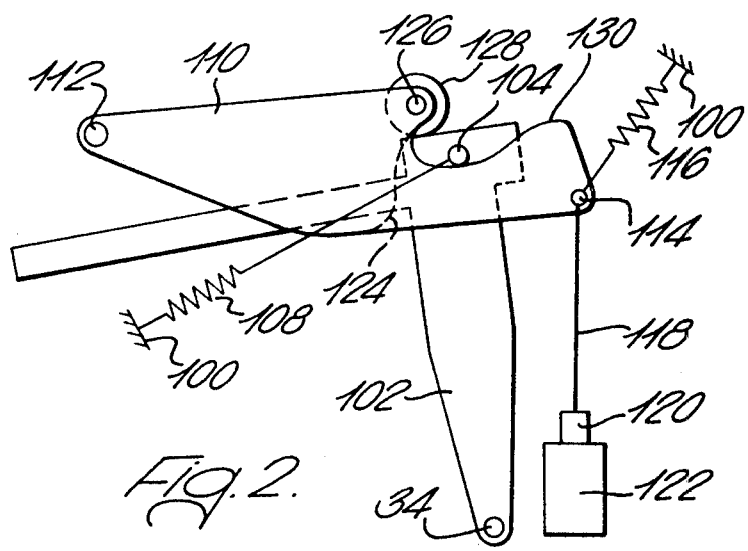
FIGS. 2 to 4 are schematic side views of a latching mechanism employed in the controller shown in FIG. 1.

Lying behind latching member 110 (as viewed in FIGS. 2 to 4) and also pivotally mounted on shaft 112 is a support bar 124 which is generally similar in configuration to latching member 110 but is shorter and terminates approximately at the line shown dotted in FIG. 2. A shaft 126 carrying a roller 128 extends between support bar 124 and latching member 110. The latching arm 102 and guide arm 106 are disposed between support bar 124 and latching member 110 and the roller 128 is capable of contacting the top surface of latching arm 102 or guide arm 106.

The operation of the latching mechanism will now be described. When the apparatus is switched off, or in the event of power failure, dangerously high drip-rate or other factor dictating that the infusion should temporarily cease (an "alarm" condition), the solenoid is switched off and the latching mechanism is as shown in FIG. 2. The plunger 120 is out of the solenoid armature, the latching arm 102 is biassed to the left by spring 108 and the latching member 110 is biassed upwardly by spring 116. In this circumstance the stub arm 38 shown in FIG. 1 compresses the tube to shut off flow of liquid to the patient (see FIG. 5).

In normal operation after start-up, the latching mechanism is as shown in FIG. 3. The solenoid is switched on and overcomes the bias of spring 116 to hold latching member 110 down. The latching arm 102 has been moved clockwise during start-up (to be described) and the bias provided by spring 108 is held against roller 128 in the shoulder formed where the top surface of guide arm 106 joins the latching arm 102. The movement of components 110 and 102 relative to their positions in FIG. 2 is shown in FIG. 3 by the arrows.

The start-up of the apparatus is illustrated with reference to FIG. 4. Upon start-up, the nurse or other operator moves the compression lever manually away from the tubing (anticlockwise in FIG. 1) and this causes the latching mechanism to take up the configuration shown in FIG. 3. The pin 104 has moved from its position shown in FIG. 2 along the latching member 110 and onto the top of the shoulder 130 to the position shown in FIG. 4. This manual action places plunger 120 within the solenoid armature so that, with the solenoid switched on, the latching member 110 is held down when the operator releases compression lever 32. This release, however, causes the latching arm 102 to move back anticlockwise to take up the position shown in FIG. 3. Note that, in moving from the FIG. 4 position on start-up to the normal running position in FIG. 3, the latching member 110 does not move substantially, and only the latching arm 102 moves anticlockwise with the roller 128 running along the top surface of guide arm 106. The purpose of a manual start-up is that it avoids the need for additional power to set the solenoid on with the plunger fully in the solenoid armature. Once the plunger has been caused to enter the armature by manual movement of the compression lever 32 as described, a lesser amount of power will hold the solenoid on.

Upon switching off the apparatus, or in the event of power failure or an alarm condition, the solenoid switches off, the bias provided by spring 116 causes latching member 110 to rise to the position shown in FIG. 2, thus causing the latching arm 102 to move anticlockwise to the position in FIG. 2 and for the compression lever 32 to cut off the liquid flow.

Figure 6:
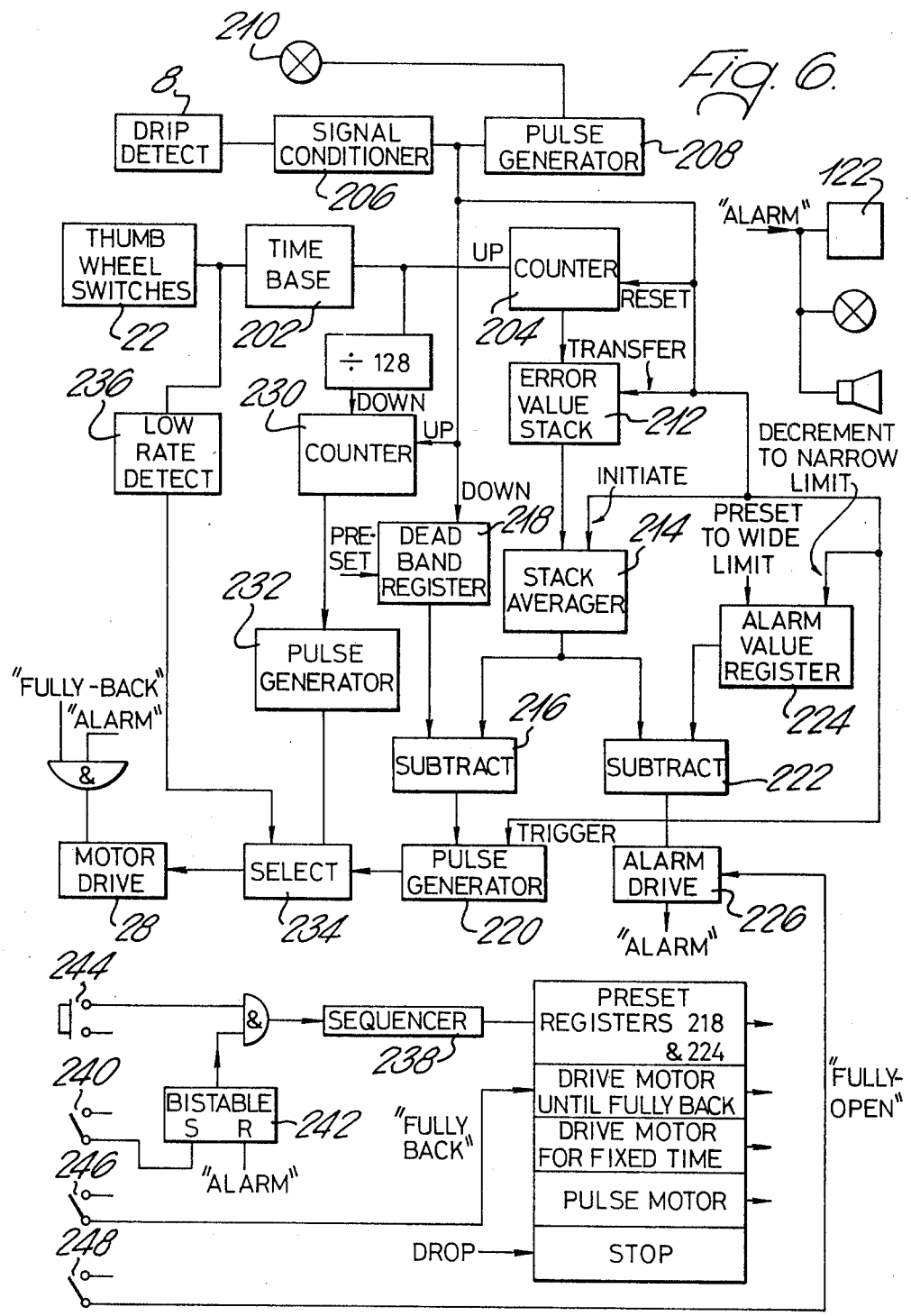
FIG. 6 is an electronic block diagram of the electronic control components of the apparatus.

The electronic processing and control means 12 is illustrated in more detail in FIG. 6 and will now be described.

The thumbwheel switches 22 program a time base generator 202 which increments a counter 204 at 128× the selected, desired drop frequency.

The drops from liquid reservoir 2 are detected by the drip-rate detector 8 and the signal from the latter, after pulse shaping by a signal conditioning circuit 206, is employed to reset counter 204 each time a drop falls. The output of circuit 206 is also employed to actuate a pulse generator 208 to drive an indicator lamp 210 whenever a drop falls.

The value held in counter 204 is transferred to an error value stack 212 prior to reset and the signal resulting from the falling of a drop initiates circuit 214 which averages the drop time over the previous 8 drops. This average value is compared by a subtraction circuit 216 with the value held by a dead band register 218. If the average value is outside the dead band value, a motor drive pulse generator 220 produces a drive pulse for the motor 28 in the appropriate direction. Each time a drop falls, the drop fall signal causes the value held by the dead band register 218 to be reduced so that control over the drip-rate becomes progressively more accurate.

The average drip-rate from circuit 214 is also supplied to circuit 222 which compares the value, by subtraction, to an alarm level value held by a register 224. If the alarm value is exceeded, the circuit is placed into the alarm condition already described and an alarm drive circuit 226 is actuated. Activation of the latter causes the solenoid of the latching mechanism already described to switch off and for an audible and visual alarm signal to be generated.

The mechanism described operates at normal drip-rates, but at low preselected drip-rates a separate control system is employed. After division by 128 in circuit 228, a counter 230 is decremented whenever a drop should fall (according to the preselected rate) and incremented whenever a drop actually falls. The state of this counter is employed to actuate a motor drive pulse generator 232, which is employed in place of the motor drive pulse generator 220. Selection of the appropriate pulse generator is by means of a selection circuit 234, which selects pulse generator 232 at low drip-rates selected at the thumbwheel switch 22, as detected by low rate detector circuit 236.

In normal operation, the pulse generator 220 provides one drive pulse per drop, with the pulse width varying with the error signal supplied by circuit 216. In low drip-rate operation, the pulse generator 232 provides a continuous drive in one direction when an error is signalled by counter 230, followed by a short reverse drive in the other direction when the counter 230 indicates that the error has been corrected.

During start-up, an initialisation procedure is selected by a sequencer 238. The compression lever 32 actuates a microswitch 240 which sets a bistable 242. If the compression lever has been operated since the last alarm condition (which resets bistable 242), the bistable 242 enables a start button 244 to commence the initialisation procedure as follows. Firstly the dead band and alarm value registers 218 and 224 are preset to initial values, then the motor 28 is operated in the forwards direction until a fully-back microswitch 246 changes state. The motor is then driven in the same direction for a fixed time interval and thereafter pulsed at a rate dependent upon the thumbwheel setting until a drop falls, whereupon the sequencer 238 ceases operation and the system described above takes over.

In an alarm condition the motor is driven backwards so as to clamp the tube against the compression lever 32 (also released by the solenoid). The drive backwards continues until a fully-back condition is detected by the fully-back microswitch 246. Should the motor drive the wheel 24 to a fully-forwards position, this is detected by a fully-forwards microswitch 248 which also actuates the alarm and also causes the motor to be driven back to the fully-back position.

The alarm value register 224 in normal operation is fed with a preselected error value for the drip-rate (which may be considered as a percentage drip-rate error) for supply to subtraction circuit 222. On initialisation a wider error value is desirable to allow the apparatus to stabilise and therefore this wider value is initially fed into register 218 but is decremented to its narrower, normal error after a short period of time.

The electronic process and control means 12 may be constructed by hard-wired logic electronic components or alternatively many of the functions may be achieved by employment of microprocessor control.

I claim:

1. An infusion drop rate controller, comprising:
   means for sensing the drip rate of liquid from an infusion liquid reservoir:
   means for selecting and storing a desired drip rate;
   means for varying the hydraulic impedance formed from a flexible tube in a flow line from said reservoir; and,
   means for controlling said varying means in response to the sensed drip rate to maintain the flow of liquid to the selected and stored drip rate, wherein the varying means comprises a cam means mounted on a shaft for compressing said flexible tube against an anvil member, the anvil member comprising a compression lever capable of movement toward and away from said cam means, whereby rotation of said shaft varies the extent of compression to vary said hydraulic impedance.

2. An infusion drop rate controller according to claim 1, further comprising fail-safe means for compressing said flexible tube in the event of abnormal operation, including power failure, such that no fluid flows through said flexible tube, the compression lever being movable into a first, off position, compressing said tube against said cam means such that no fluid flows through said flexible tube and, into a second, operating position wherein said lever does not prevent fluid to flow through said tube.

3. An infusion drop rate controller according to claim 2, further including means for maintaining said compression lever in said second position during normal operation and means for urging said compression lever into said first, off position on release of said maintaining means.

4. An infusion drop rate controller according to claim 3, wherein said maintaining means comprises latch means.

5. An infusion drop rate controller according to claim 4, wherein said latch means comprises a latch arm and a solenoid, said solenoid, when energised, causing said latch arm to maintain said compression lever in said second position, and when de-energised, allowing said compression lever to be urged into said first, off position.

6. An infusion drop rate controller according to claim 4, wherein said latch means is controlled by said controlling means.

7. An infusion drop rate controller according to claim 1, wherein said cam means comprises a wheel mounted eccentrically on said shaft and whose circumferential surface contacts said tube.

8. An infusion drop rate controller according to claim 2, wherein in the second, operating position, the lever contacts but does not substantially compress said tube.

9. An infusion drop rate controller according to claim 4, wherein said controlling means comprises means for sensing abnormal operation which, on sensing abnormal operation, controls at least one of said latch means and said cam means to cause compression of said flexible tube such that no fluid flows through the flexible tube.

10. An infusion drop rate controller according to claim 1 wherein said means for sensing the drip rate includes optical means including a light source, and means responsive to the light source whereby to provide an electrical signal modulated by the drops of liquid interrupting a light beam extending between said light source and said electrical signal providing means.

11. An infusion drop rate controller according to claim 1, further comprising a time base means which provides a time base of frequency in relationship to the drip rate held by the drip rate selecting and storing means, means for comparing signals from said time base means to signals provided by the drip rate sensing means and means for controlling said varying means in response to said comparing means.

12. An infusion drop rate controller according to claim 11 wherein said comparing means provides error signals dependent upon the difference between said time base signals and said signals from the drip rate sensing means and wherein said controller includes an error valve store and means for comparing said error signals to signals provided by said error value store and for actuating said varying means in response thereto.

13. An infusion drop rate controller according to claim 1, further comprising means for detecting whether a present low drip rate has been selected and is held by said drip rate selecting and storing means, and means responsive to said low drip rate detecting means for actuating a low drip rate control means for controlling said varying means at said low drip rates.

14. An infusion drop rate controller, comprising:
means for sensing the drip rate of liquid from an infusion liquid reservoir;
means for selecting and storing a desired drip rate;
means for varying the hydraulic impedance formed from a flexible tube in a flow line from said reservoir;
means for controlling said varying means in response to the sensed drip rate to maintain the flow of liquid to the selected and stored drip rate, wherein the varying means comprises a cam means mounted on a shaft for compressing said flexible tube against an anvil member whereby rotation of said shaft varies the extent of compression to vary said hydraulic impedance;
means for detecting whether a preset low drip rate has been selected and is held by said drip rate selecting and storing means; and,
means responsive to said low drip rate detecting means for actuating a low drip rate control means for controlling said varying means at said low drip rates.

* * * * *